US006681131B2

(12) United States Patent
Kandori et al.

(10) Patent No.: US 6,681,131 B2
(45) Date of Patent: Jan. 20, 2004

(54) APPARATUS FOR MEASURING BIO-MAGNETIC FIELDS

(75) Inventors: Akihiko Kandori, Kokubunji (JP); Tsuyoshi Miyashita, Fuchu (JP); Daisuke Suzuki, Kodaira (JP); Koichi Yokosawa, Kodaira (JP); Keiji Tsukada, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 298 days.

(21) Appl. No.: 09/977,213

(22) Filed: Oct. 16, 2001

(65) Prior Publication Data

US 2002/0062076 A1 May 23, 2002

(30) Foreign Application Priority Data

Oct. 19, 2000 (JP) .......................................... 2000-324685

(51) Int. Cl.[7] ................................................ A61B 5/05
(52) U.S. Cl. ........................ 600/409; 324/248; 324/244
(58) Field of Search ................................ 600/409, 408, 600/407, 410, 411, 413, 425, 428, 509, 544; 324/244, 248, 260; 702/189–190; 505/846

(56) References Cited

U.S. PATENT DOCUMENTS

| 5,204,624 | A | * | 4/1993 | Ueda ........................... 324/248 |
| 6,230,037 | B1 | | 5/2001 | Tsukada et al. |
| 6,336,043 | B1 | * | 1/2002 | Suzuki et al. ................. 600/409 |
| 6,473,518 | B1 | * | 10/2002 | Machida et al. ............. 382/128 |
| 6,539,245 | B2 | * | 3/2003 | Tsukada et al. ............. 600/409 |
| 6,609,019 | B1 | * | 8/2003 | Teshigawara et al. ....... 600/409 |
| 2002/0045813 | A1 | * | 4/2002 | Suzuki et al. ................. 600/409 |
| 2003/0097056 | A1 | * | 5/2003 | Suzuki et al. ................. 600/409 |

FOREIGN PATENT DOCUMENTS

| JP | 6-225860 | 12/1993 |
| JP | 11-099133 | 9/1997 |

OTHER PUBLICATIONS

W.G. Kubicek, J.N. Karnegis, R.P. Patterson, D.A. Witsoe and R.H. Mattson, "Development and Evaluation of an Impedance Cardiac Output System," Aerospace Medicine, Dec. 1966, pp. 1208–1212.

David G. Newman and Robin Callister, "The Non-Invasive Assesment of Stroke Volume and Cardiac Output by Impedance Cardiography: A Review," Aviation, Space and Environmental Medicine, vol. 70, No. 8 (Aug. 1999), pp. 780–789.

* cited by examiner

Primary Examiner—Eleni Mantis Mercader
(74) Attorney, Agent, or Firm—Reed Smith LLP; Stanley P. Fisher, Esq.; Juan Carlos A. Marquez, Esq.

(57) ABSTRACT

An apparatus for measuring bio-magnetic fields includes a plurality of magnetometers for detecting magnetic fields generated from a live body; a driving circuit for driving the magnetometers; a computer for collecting output signals of the driving circuit in the form of data representing at least one waveform of the magnetic fields generated from the live body and for performing an arithmetic processing on the data representing the waveform of magnetic fields, a display unit, and at least one signal processing circuit for processing output signals of the driving circuit. The computer further performs an arithmetic processing of first-order differentiation on the waveform of the magnetic fields in a z direction with respect to time in order to create an arrow map and a contour map. The apparatus can also detect mechanical movement which occurs as blood flows in organs and organs move.

20 Claims, 14 Drawing Sheets

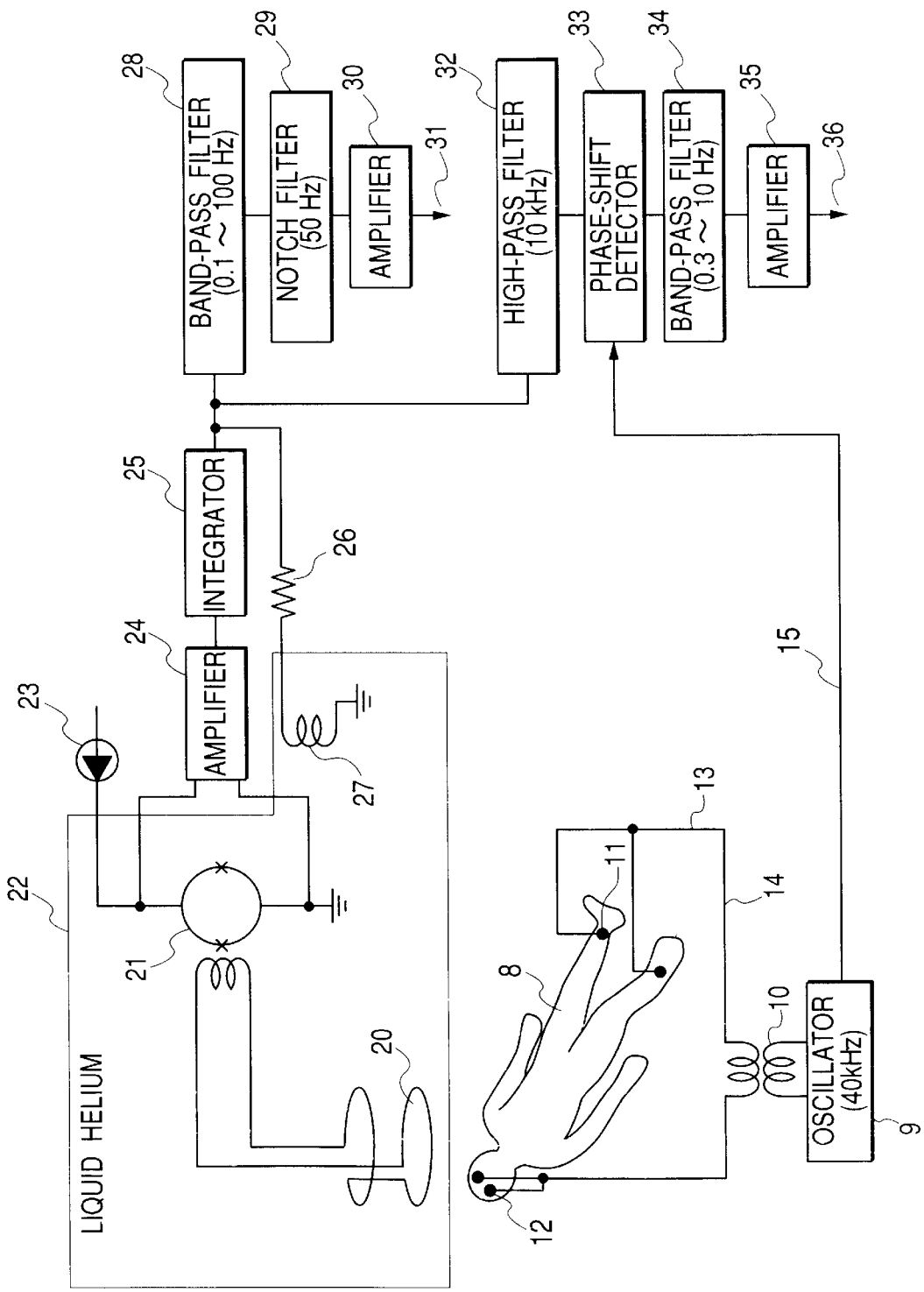

901

902

APPARATUS FOR MEASURING BIO-MAGNETIC FIELDS

BACKGROUND OF THE INVENTION

1. Field of the Invention

The present invention relates to an apparatus for measuring bio-magnetic fields by using SQUID (Superconducting Quantum Interference Device) magnetometers or the like to detect weak magnetic fields generated from the heart or brain of an adult, an infant, or a fetus. More particularly, the present invention relates to an apparatus for measuring the bio-magnetic fields detects in real time changes of the magnetic fields of the live body when a high-frequency AC current is applied to the body and for calculating and displaying the changes in a two-dimensional map.

2. Description of the Related Arts

The conventional ways for measuring bio-magnetic fields include detecting the changes of magnetic fields caused by neuron actions in brain cells, which provides magneto-encephalograms, or by electric current activated in cardiac muscle cells, which provides magneto-cardiograms.

A new method named "impedance cardiograph" is designed to measure the electric potential changes, that appears as the amount of blood flowing in a live animal body or a human body of an adult, an infant, or a fetus, when the body is subjected to a high-frequency AC current. (Aerospace Medicine, vol. 37, pp. 1208–1212 (1966), Aviation, Space, and Environmental Medicine, vol. 70, No. 8, 780–789 (1999).

The Japanese Patent Laid-open No. 225860/1994 discloses an apparatus for measuring the spatial distribution of electric impedance. This apparatus supplies electric current to a to-be-examined region in the live body through at least two electrodes and electric wires so as to trigger impedance and current which distribute corresponding to the positions of the electrodes, thereby detect the spatial distribution of the characteristic quantities of the magnetic field generated by the current distribution at measuring points outside the to-be-examined region by means of a magnetic field measuring apparatus, and reconstructs the equivalent current density distribution inside the to-be-examined region from the spatial distribution of the characteristic quantities. The apparatus is thus highly sensitive to the magnetic fields generated by electric wires in the to-be-examined region by using a compensation conductive loop.

The above-mentioned apparatus regarding magneto-encephalograms and magneto-cardiograms share one disadvantage that they merely monitor the electric phenomena in cells but not the two-dimensional mechanical movement of the heart magnetic fields. Another disadvantage of the conventional impedance cardiograph based on potential measurements is the use of a large number of electrodes for monitoring the blood flowing in the region, which is undesirable for general use, such as clinical diagnostic.

For these reasons, there has been a demand for a technique for monitoring in real time and in a non-contacting manner the magnetic fields which change along with the mechanical movements of blood flow, cardiac contraction and expansion, or the like. There has also been a demand for a technique for measuring in real time the mechanical movement of blood simultaneously with the electrical activity of cardiac muscle and brain thereby drawing a two-dimensional map.

The Japanese Patent Laid-open No. 225860/1994 discloses a technique for detecting the distribution of electric impedance at a certain time created by the electric current flowing in the live body through the electrodes, but it does not detect in real time the change of electrical impedance.

OBJECT AND SUMMARY OF THE INVENTION

It is an object of the present invention to provide an apparatus for measuring bio-magnetic fields of a live body. The apparatus is designed to measure the magnetic field from the heart or the magnetic field from the brain which is generated by the electrical activity of muscles and nerve cells in the live body and to detect simultaneously the mechanical movement induced by the blood flow in organs or the movement of organs in the live body,—so as to monitor them in real time in a two-dimensional manner.

In order to more clearly and concisely describe the subject matter of the claims, the following terms are intended to provide guidance as to the meanings of specific terms used in the following written description. Also it is to be understood that the phraseology or terminology employed herein is for the purpose of description and not of limitation. As used herein:

"Cardiac magnetic field" denotes the magnetic field generated by the electric activity of cardiac muscles. This magnetic field can be detected by a SQUID magnetometer or the like.

"Magneto-cardiogram waveform (MCG)" denotes the waveform of a cardiac magnetic field.

"Magneto-cardiogram (MCG map)" denotes a two-dimensional contour map of a cardiac magnetic field (an magnetic field distribution map of contour lines formed by connecting points having an equal magnetic field magnitude).

"Impedance cardiac magnetic field" denotes a magnetic field generated from the high-frequency AC current applied to a live body. This magnetic field is detected by a SQUID magnetometer or the like.

"Impedance magneto-cardiogram waveform (I-MCG)" denotes the waveform of an impedance cardiac magnetic field.

"Impedance magneto-cardiogram (I-MCG map)" denotes a two-dimensional contour map of the impedance cardiac magnetic field (an magnetic field distribution map of contour lines formed by connecting points having an equal magnetic field magnitude).

According to one embodiment of the present invention, the apparatus for measuring bio-magnetic fields comprises a plurality of SQUID magnetometers (which are arranged in a cryostat maintained in a superconducting state) for detecting the magnetic fields generated from the live body, and driving circuits for driving the SQUID magnetometers. The apparatus is connected to electrodes which are attached to more than one point of the subject under examination, such as the head, leg, etc. The high-frequency AC current generated from a signal generator, such as an oscillator, is supplied to the electrodes. The output signals of the driving circuits are processed by two signal processing circuits.

The first signal processing circuit includes a band-pass filter, a notch filter, and an amplifier. The second signal processing circuit includes a high-pass filter, a phase-shift detector, a band-pass filter, and an amplifier.

The output signal (I-MCG) from the second signal processing circuit is displayed on a display unit in correspondence with each position where a detecting coil of the SQUID magnetometer is arranged.

The magneto-cardiogram (NCG map) and the impedance magneto-cardiogram (I-MCG map) are obtained by processing with a computer based upon the magneto-cardiogram waveform (MCG) and the impedance magneto-cardiogram waveform (I-MCG) at an arbitrary time.

The output signal (MCG) from the first signal processing circuit and/or the output signal (I-MCG) from the second signal processing circuit may be displayed on a display unit in correspondence with each position where a detecting coil of the SQUID magnetometer is arranged.

More than one I-MCG may be displayed (ex. in an overlapping manner) on a display unit. Likewise, more than one MCG may be displayed on a display unit.

The impedance magneto-cardiogram (I-MCG map) obtained from the output signal (I-MCG) of the second signal processing circuit may be displayed on a display unit simultaneously with the MCG map obtained from the output signal (MCG) of the first signal processing circuit.

By using signals triggered by a waveform of the electrocardiogram (obtained by an electrocardiograph) which is measured simultaneously with the magneto-cardiogram waveform (MCG) and the impedance magneto-cardiogram waveform (I-MCG) or the R-wave of the magneto-cardiogram waveform (MCG), the computer performs an averaging process for the impedance magneto-cardiogram waveform (I-MCG), and an arithmetic processing of first-order differentiation on the impedance magneto-cardiogram waveform (I-MCG) with respect to time so as to provide at least one waveform of the magnetic fields due to first-order differential. The computer further processes the waveform to provide a contour map (a chart showing the distribution of equal magnetic field magnitudes) in which points of equal first-order differential values at an arbitrary time are connected. The resulted map is displayed on a display unit.

Moreover, the computer processes the waveform of first-order differential of magnetic field magnitudes to reconstruct the distribution of electric current or the distribution of conductivity (or resistivity) in the live body at an arbitrary time. The distribution thus obtained is displayed as a two-dimensional or three-dimensional pattern on a display unit.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein:

FIG. 3 is a circuit diagram of the embodiment shown in FIG. 1;

FIG. 4 shows waveforms measured in the embodiment shown in FIG. 1, wherein

FIG. 7 shows two-dimensional contour maps obtained from the impedance magneto-cardiogram waveforms (I-MCG) shown in FIGS. 5 and 6, wherein

FIG. 9 shows the display images in the embodiment shown in FIG. 1, wherein

FIG. 10 illustrates how the arrangement of electrodes affects impedance magneto-cardiogram waveforms (I-MCG), wherein

DESCRIPTION OF THE PREFERRED EMBODIMENTS

Figure 1:
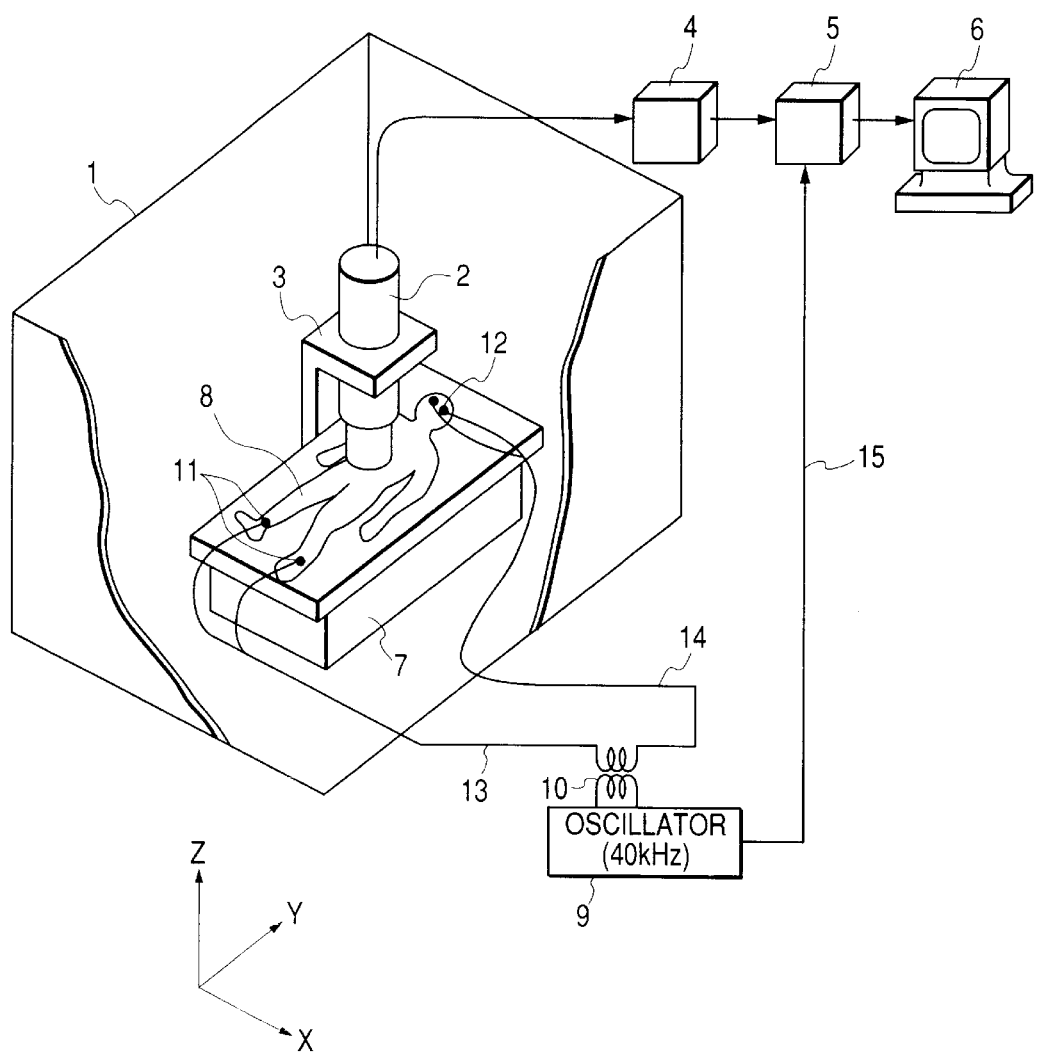
FIG. 1 is a diagram showing an embodiment of the invention.

A preferred embodiment of the present invention measures at 64 points a magnetic field ($B_z$) in the direction (z direction) perpendicular to the front surface of the live body. The points for measurements correspond to the positions of the detecting coils of first-order differential type SQUID magnetometer which are projected onto the front surface of the live animal body. The magnetic field measured is represented by $B_z(x, y, t)$, where $(x, y)$ denotes the coordinates of each point of measurement and t denotes the time of taking the measurement. $B_z(x, y, t)$ is abbreviated as $B_z$ hereinafter. Incidentally, the current arrow vector $(I_x, I_y)$ discussed later has the components $I_x$ and $I_y$ which vary with $(x, y)$ and t and are represented with $I_x(x, y, t)$ and $I_y(x, y, t)$, which are abbreviated as $I_x$ and $I_y$ hereinafter.

EXAMPLE 1

This example demonstrates an apparatus for measuring the bio-magnetic fields of the live body. The apparatus includes a plurality of SQUID magnetometers for detecting the magnetic fields generated from the live body, a driving circuit for SQUID magnetometers, a computer for collecting output signals of the driving circuit (as data representing waveforms of the magnetic field generated from the live body) and for processing the data representing the waveforms of the magnetic fields, a display unit for displaying the results of the processing, a first and a second signal processing circuits for outputting signals of the driving circuit, and a signal generator for generating a high-frequency AC current to be applied to the live body.

The subject under examination has electrodes attached at several spots on the front surface so as to apply high-frequency AC current to the front surface. Such high-frequency AC current supplied from the signal generator enters the subject through the electrodes. Incidentally, the electrodes are arranged on the head and both legs of the body.

The first signal processing circuit has a first band-pass filter for passing the portions of the output signals of the driving circuit falling within a first predetermined bandwidth, a filter for removing a predetermined frequency component from the output signals of the first band-pass filter, and a first amplifier for amplifying the output signals of the filter.

The second signal processing circuit has a high-pass filter for passing the portions of the output signals of the driving circuit falling with frequencies above a predetermined value, a phase-shift detector for demodulating the portions with the frequency of the signal generator from the output signals of the high-pass filter, a second band-pass filer for passing the portions of the output signals of the phase-shift detector falling within a second predetermined bandwidth, and a second amplifier for amplifying the output signals of the second band-pass filter.

At least one of the output signals of the first and second signal processing circuits and the output signals of the electrocardiograph are displayed on the display unit. The output signals of the second signal processing circuit are displayed on the displaying unit corresponding to the measuring positions where the SQUID magnetometers are arranged.

The computer usually performs arithmetic processing in the following manners, and the display unit usually displays the results of arithmetic processing in the following manner.

(I) The computer performs an averaging process on the output signals of the second signal processing circuit. At each measuring point, the second signal processing circuit outputs the signals of repetitive waveforms, which are added then divided by the number of the repetitive waveforms happening in a period of time. The starting time of the period is determined based on (a) the trigger signal of R-wave in Lead II ECG measured at the same time or based on (b) the trigger signal of R-wave in MCG measured at the same time (which is output signals of the first signal processing circuit and is formed by the repetitive waveforms). The computer partially differentiates the magnetic field $B_z$ (the output signals of the second signal processing circuit) with respect to x and y, while $B_z$ is measured in the normal direction (z direction) by a plurality of SQUID magnetometers. The resulted partial differentials $\partial B_z/\partial x$ and $\partial B_z/\partial y$ are used to calculate $\sqrt{(\partial B_z/\partial x)^2+(\partial B_z/\partial y)^2}$. The computer draws a contour map (showing the distribution of equal magnetic field magnitudes) by connecting points of equal $\sqrt{(\partial B_z/\partial x)^2+(\partial B_z/\partial y)^2}$ values at a predetermined time. Alternatively, the display unit vectorially displays the current (in arrows) in the (x, y) plane at a predetermined time. The x component of each current arrow is $I_x=\{\partial B_z/\partial x\}$ and the y component of the current arrow is $I_y=-\{\partial B_z/\partial y\}$. The computer performs arithmetic processing to generate the arrow map (current distribution diagram) by connecting points of equal current magnitude in arrows $[I_{xy}=\sqrt{(I_x^2+I_y^2)}]$ in an overlapping manner on the (x, y) plane. The display unit selectively displays at least one of the contour map and the current arrow map. The computer performs arithmetic processing to estimate the position of electric current dipole from the obtained contour map. The display unit displays the position and magnitude of the electric current dipole together with the contour map. Using the obtained contour map, the computer performs arithmetic processing to estimate the distribution of conductivity in the live body to be displayed on the display unit.

(II) By using output signals obtained from the second signal processing circuit, the computer performs first-order differentiation with respect to time on the waveform of magnetic field $B_z$ measured in the normal direction (z direction) by a plurality of SQUID magnetometers and then performs arithmetic processing to obtain the waveform of first-order derivatives of the magnetic fields. More than one waveform may be displayed in an overlapping manner.

(III) By using output signals obtained from the second signal processing circuit, the computer performs first-order differentiation with respect to time on the waveform of magnetic field $B_z$ measured in the normal direction (z direction) by a plurality of SQUID magnetometers, and then performs arithmetic processing to obtain the contour map by connecting points of equal first-order derivatives of the magnetic fields at a predetermined time. The display unit displays the resulted contour map.

(IV) By using output signals obtained from the second signal processing circuit, the computer performs first-order differentiation with respect to time on the waveform of magnetic field $B_z$ measured in the normal direction (z direction) by a plurality of SQUID magnetometers, the computer performs arithmetic processing to obtain the waveform of first-order derivative of magnetic field $B_z'$ with respect to time, the computer performs partial differentiation with respect to x and y on the waveform of first-order derivative of magnetic field $B_z'$ and the computer calculates $\sqrt{(\partial B_z'/\partial x)^2+(\partial B_z'/\partial y)^2}$ from $\partial B_z'/\partial x$ and $\partial B_z'/\partial y$ so as to draw a first contour map by connecting points of equal $\sqrt{(\partial B_z'/\partial x)^2+(\partial B_z'/\partial y)^2}$ values at a predetermined time. Alternatively, the computer performs arithmetic processing to vectorially show the current in arrows in the (x, y) plane at a predetermined time. The x component of each current arrow is $I_x'=\{\partial B_z'/\partial x\}$ and the y component of each current arrow is $I_y'=\{-\partial B_z'/\partial y\}$. The computer further performs arithmetic processing to provide a second map contour lines obtained by connecting points of equal $[I_{xy}'=\sqrt{(I_x')^2+(I_y')^2}]$ values on the (x, y) plane. The display unit selectively displays at least one of the first map and the second map. The computer performs arithmetic processing to estimate the electric current dipole from the first map (corresponding to the contour map or distribution of equi-magnetic fields). The display unit displays the position and magnitude of electric current dipole together with the contour map. Using the obtained contour map, the computer performs arithmetic processing to estimate the distribution of conductivity in the live animal body to be displayed on the display unit.

EXAMPLE 2

This example demonstrates another embodiment of the invention. This embodiment differs from that of Example 1 in the construction of the signal processing circuit (i.e., the signal processing circuit consists of the second signal processing circuit only). The apparatus of this example includes a plurality of SQUID magnetometers for detecting the magnetic field generated from the live body, a driving circuit for driving the SQUID magnetometers, a computer for collecting output signals of the driving circuit (as data representing waveforms of the magnetic field generated from the live body) and for processing the data representing the waveforms of the magnetic field, a display unit for displaying the results of the processing, a signal processing circuit for outputting signals of the driving circuit, and a signal generator for generating a high-frequency AC current to be applied to the live body, and an electrocardiograph to give electrocardiograms.

Electrodes are attached to a human body at several places on the front surface of the body so as to apply high-frequency AC current to the body. High-frequency AC current supplied from the signal generator enters the subject through the electrodes. Incidentally, the electrodes are arranged on the head and both legs of the body.

The signal processing circuit has a high-pass filter for passing the portions of the output signals of the driving circuit falling with frequencies above a predetermined value, filter for passing a phase-shift detector for demodulating the portions with frequency of the signal generator from the output signals of the high-pass filter, a band-pass filer for passing the portions of the output signals of the phase-shift detector falling within a predetermined bandwidth, and an amplifier for amplifying the output signals of the band-pass filter. The output signals of the signal processing circuit are displayed on the display unit.

There is a difference between Example 1 and Example 2 in the computer arithmetic processing which results then are displayed on the display unit. measurements. In Example 2, the computer performs the averaging process on the output signals of the signal processing circuit based on Lead II ECG measured at the same time. At each measuring point, the signal processing circuit outputs the signals of repetitive waveforms, which are added then divided by the number of repetitive waveforms collected within a time period. The starting time of the period is determined based measurements on the trigger signal of R-wave in Lead II ECG. The description in (I) to (IV) is also applicable in Example 2 by eliminating "the first signal processing circuit" and substituting "the second signal processing circuit" with "the signal processing circuit".

The first and second examples of the present invention will be described in details with reference to the accompanying drawings. First, the high-frequency current to be applied to the live body is discussed.

The electrical property of living tissues is designated as α-dispersion, β-dispersion, and γ-dispersion in the order of increasing frequencies. Frequencies of the order of 10 k to MHz are within the region of the β-dispersion, which is most used because it is safe for the live body. High-frequency current having frequencies within the region of the β-dispersion produces magnetic fields represented by the equations (1) to (4). E denotes the electric field, J denotes the electric current density, B denotes the magnetic flux density, $\mu_0$ denotes the permeability of vacuum, D denotes the displacement current, σ denotes the electric conductivity of the live animal body, and t denotes the time variable.

$$\text{rot } E = 0 \quad (1)$$

$$\text{div } J = 0 \quad (2)$$

$$\text{rot } B = \mu_0 J \quad (3)$$

$$J = \sigma E + dD/dt \quad (4)$$

Equation (4) can be modified into equation (5) by denoting that an imaginary unit with j, an angular frequency with ω, a permittivity of vacuum with $\epsilon_0$, a relative permittivity with $\epsilon_r$, and D=exp(jωt).

$$\begin{aligned} J &= \sigma E + j\omega D \\ &= \sigma E + j\omega \epsilon_r \epsilon_0 E \\ &= \sigma(1 + j\omega \epsilon_r \epsilon_0 / \sigma)E \end{aligned} \quad (5)$$

The displacement current is calculated by the equations (6) and (7), assuming that the conductivity of the live animal body σ=0.3 (S/m) and the relative permittivity of the live animal body $\epsilon_r = 10^4$.

$$\omega \epsilon_r \epsilon_0 / \sigma = 2\pi \times 40 \times 10^3 \times 10^4 \times 8.85 \times 10^{-12}/0.3 = 0.074 \quad (6)$$

$$\omega \epsilon_r \epsilon_0 / \sigma \ll 1 \quad (7)$$

Since it is apparent from the equations (6) and (7) that the displacement current is negligibly small, the equation (4) can be rewritten as the equation (8).

$$J = \sigma E \quad (8)$$

Also, the equation (1) can be rewritten as the equation (9) wherein V denotes potential.

$$E = -\text{grad } V \quad (9)$$

The equation (10) is then derived from the equations (2), (3), (8), and (9). The equation (10) turns into the equation of the Biot-Savart law if the conductivity is constant.

$$\text{rot } B = \mu_0 \sigma(-\text{grad } V) \quad (10)$$

Therefore, if the electric field or potential is constant, the change in magnetic field induced by a flow of high-frequency current depends on the electric conductivity (σ) which varies with position (r) and time (t).

According to the present invention, the apparatus for measuring bio-magnetic fields is constructed as shown in FIG. 1. In a magnetically shielded room 1, a bed 7 on which the subject 8 lies down, a cryostat 2, and a gantry to mechanically hold the cryostat 2 are disposed. The cryostat holds a coolant, such as liquid helium and liquid nitrogen, to keep the SQUID magnetometers in a superconducting state. The bed is movable in three directions (x, y, z).

A circuit 4, an amplifier filter unit 5, and a computer 6 are placed outside the shielded room. The circuit 4 is designed to drive SQUID magnetometers. The amplifier filter unit 5 contains a phase detecting circuit for detecting signal components having higher frequencies than the frequency band of the magnetic fields generated from heart or brain of the live body. The computer 6 receives output signals (data) of the amplifier filter unit 5 and performs computation processing on the signals. The computer 6 has a display unit for displaying the results of processing.

The amplifier filter unit 5 has a high-pass filter 32 (for 10 KHz), a phase-shift detector 33, a band-pass filter 34 (for 0.3–10 Hz), and an amplifier 35, as shown in FIG. 3. The high-pass filter 32 passes the portions of the than output the signals of the driving circuit with frequencies above a predetermined value. The phase-shift detector 33 demodulates the sideband of the center frequency of the signal generator from the output signals of the high-pass filter 32. The oscillator 9 and the phase-shift detector 33 are connected through the signal wire 15.

The band-pass filter 34 preferably has a cut-off frequency of 0.3 Hz so as to remove variance due to the breath of the subject (usually lower than 0.2 Hz). The phase-shift detector 33 for synchronizing with the frequency of the reference signals from the oscillator 9. Such reference signals include the output voltage of the oscillator and the high-frequency current actually flowing through the subject 8, or voltage across a resistor connected in series to the electric wire 13 or 14. To protect the subject from electrical shocks, the oscillator is electrically isolated from earth by a transformer 10.

To provide a noiseless high-frequency current from the oscillator 9 to the subject, the output of the oscillator is supplied to the electric wires 13 and 14 through a band-pass filter.

The embodiment shown in FIG. 1 employs the magnetically shielded room 1 in which magnetic fields generated from the live body ("subject") are measured. The magnetically shielded room 1 is not necessary if the measurements are carried out under magnetically favorable conditions or in other actively-shielded environments, or if the measurements are carried out by means of high-order differentiating coils. Whenever the SQUID magnetometers are subject to high-frequency interference, they should be installed in an electromagnetic shielding room.

Figure 2A:
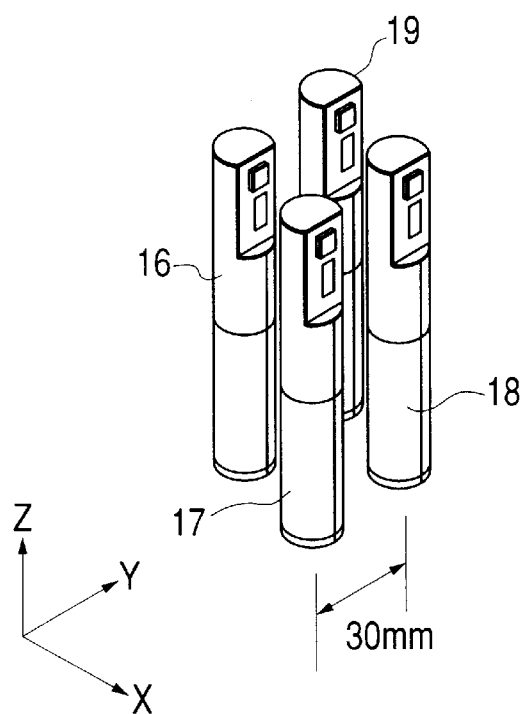
FIG. 2A is a diagram showing the arrangement of SQUID magnetometers for measuring weak magnetic fields generated from a human heart in the embodiment shown in FIG. 1.

In the embodiment of the present invention, the SQUID magnetometers 16, 17, 18, 19 for measuring the weak magnetic fields generated from the heart are arranged as shown in FIG. 2A. Each magnetometer is equipped with a first-order differential type pickup coil to measure the magnetic field ($B_z$) in z direction perpendicular to the surface of the body, i.e. the "x, y" plane. The pickup coil is made of a superconducting wire. The base line of pickup coil is 50 mm and the diameter of the pickup coil is 18 mm.

The four SQUID magnetometers are arranged in a 2×2 array as shown in FIG. 2A, with the distance of two magnetometer centers being 30 mm. The array is not limited to 2×2 magnetometers, and it may range from 3×3 magnetometers to 8×8 magnetometers.

Figure 2B:
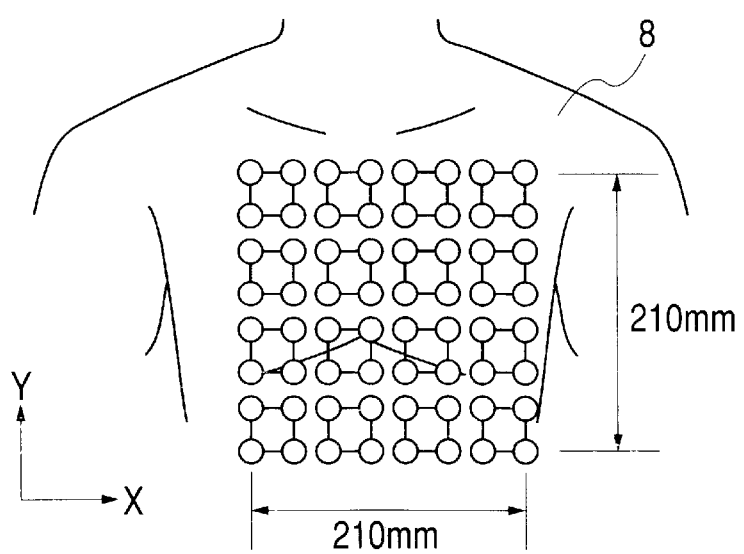
FIG. 2B is a diagram showing a to-be-measured region on a human body.

FIG. 2B schematically shows the area (210×210 mm) that can be scanned by the four SQUID magnetometers shown in FIG. 2A. The four SQUID magnetometers are positioned as shown in FIG. 2B by moving the bed 7 on which the subject 8 lies down with the face up. The magnetic fields at 64 points are measured.

In the embodiment of the present invention, the apparatus for measuring bio-magnetic fields generated from the living body is constructed as shown in FIG. 3. The apparatus has four electrodes. Two electrodes 11 are attached the ankles of the subject 8, and two electrodes 12 are attached to the forehead of the subject 8 with the same contacting area. The ankles and forehead are suitable for electrodes because they permit the high-frequency current to flow uniformly through the body with least interference by the breath of the subject which may disrupt the contacts between the electrodes and the subject.

Another advantage of attaching the electrodes to the forehead and ankles is to keep the SQUID magnetometers as far away from the electrodes as possible so that they are less affected by the magnetic fields generated by the high-frequency current flowing through the electric wires 13 and 14.

It is desirable that the electrodes 11 and 12 are attached to the skin degreased with alcohol and coated by an electrically conductive cream. The electrodes 11 and 12 are preferably non-magnetic aluminum electrodes or disposable carbon electrodes (which are used in this embodiment).

The electrodes 11 and 12 have two lead wires 13 and 14 which are electrically connected to an oscillator 9 via a transformer 10. The oscillator generates high-frequency current, 40 KHz and 1 mA$_{p\text{-}p}$, to be applied to the subject. The frequency of the current to be applied to the subject will be discussed in details later. The high-frequency current generates the impedance cardiac magnetic fields, which, together with the cardiac magnetic fields generated by the electrical activity of the cardiac muscles, are detected by a pickup coil 20. The pickup coil 20 usually works with a gradiometer or a magnetometer of axial type for detecting a magnetic field perpendicular to or parallel with the body surface.

The detected cardiac magnetic field and impedance cardiac magnetic field are converted into voltages by the SQUID 21. The SQUID magnetometer becomes active when it is biased by a DC source 23. The magnetic field detected by the SQUID is linearly converted into voltage by means of an amplifier 24, an integrator 25, a feedback resistance 26, and a feedback coil 27. The pickup coil 20, SQUID 21, and feedback coil 27 are arranged in a cryostat 22 filled with liquid helium.

The integrator 25 is connected to two processing circuits which process the output signals from the integrator 25 simultaneously and output two output signals 31 and 36. The first processing circuit comprises a band-pass filter 28 (0.1 Hz–100 Hz), a notch filter 29 to remove 50 Hz component, and an amplifier 30. It gives a waveform of the ordinary cardiac magnetic field (MCG) 31.

The second processing circuit comprises a high-pass filter 32 (10 KHz), a phase-shift detector 33, a band-pass filter 34 (0.3 Hz–10 Hz), and an amplifier 35. The high-pass filter 32 has a cut-off frequency which is lower than the frequency of the high-frequency current flowing through the subject, and it extracts modulated signals only. The phase-shift detector 33 demodulates the side band of the center frequency of the oscillator from the output signals of the high-pass filter 32. The oscillator and the phase-shift detector are connected through a signal wire 15.

The band-pass filter 34 preferably has a cut-off frequency of 0.3 Hz so as to remove variance due to the breath of the subject (usually lower than 0.2 Hz). The phase-shift detector 33 for synchronizing with the frequency of the reference signals from the oscillator 9. Such reference signals include the output voltage of the oscillator and the high-frequency current actually flowing through the subject 8, or voltage across a resistor connected in series to the electric wire 13 or 14. To protect the subject from electrical shocks, the oscillator is electrically isolated from earth by a transformer 10.

To provide noiseless high-frequency current from the oscillator 9 to the subject, it is desirable to transmit the output from the oscillator to the electric wires 13 and 14 through a band-pass filter.

The SQUID magnetometer has an FLL (flux-locked loop) circuit whose bandwidth f is calculated from the equation (11) below.

$$f=(dV/d\Phi) \times G \times f_{int} \times \beta \qquad (11)$$

where, (dV/dΦ) denotes the effective flux-voltage conversion ratio of the SQUID, G denotes the gain of the initial-stage amplifier, $f_{int}$ denotes the bandwidth of the integrator, and β denotes the feedback rate of the feedback loop.

The bandwidth f should be higher than the frequency of the high-frequency current flowing through the subject. In this embodiment, the bandwidth f is 138 KHz, which is obtained by the equations as follows.

$$(dV/d\Phi)=440 \ (V/\Phi_0)$$

$$G=600$$

$$F_{int}=16 \ (kHz)$$

$$\beta=33 \ (\Phi_0/V)$$

where $\Phi_0$ is a flux quantum of $2.07 \times 10^{-15}$ Wb

The high-frequency current with a frequency of 40 KHz, which is within the region of β-dispersion, produces the skin effect in the live body which is represented by $1/\sqrt{(\omega\sigma\mu)}$ and calculated from the equation (12) below.

$$1/\sqrt{(\omega\sigma\mu)}=1/\{\sqrt{(2\pi \times 4 \times 10^4 \times 0.3 \times 4\pi \times 10^{-7})}\}=3.2 (m) \qquad (12)$$

where, $\mu$ denotes the permeability of the living body, which is set hereinafter to be equal to the permeability of vacuum $\mu_0 = 4\pi \times 10^{-7}$.

The effective length of the skin effect is much longer than the body length, which allows the high-frequency current uniformly flows though the subject.

The above-mentioned results are derived under an assumption that the high-frequency current to be applied to the subject has a frequency of 40 KHz, which has been assumed in the equation (12). If the frequency is 10 KHz or 100 KHz, the skin effect will be 6.5 m or 2.1 mm, respectively, which are much longer than the average human body length. Therefore, high-frequency current having a frequency from 10 KHz to 100 KHz is satisfactory to flow uniformly through the subject.

The SQUID magnetometer has a sensitivity of 18 nT/V. The sensitivity is defined as the ratio of magnetic field strength to voltage(dB/dV). The maximum current to be measured without saturating the circuit voltage is calculated by a simple model of a single conductor carrying current. The magnetic field generated by current flowing through an infinitely long conductor is represented by Ampere's law (equations 13 and 14) as follows.

$$B = \mu_0 I_{max}/(2\pi r) \quad (13)$$

$$I_{max} = 2\pi r B/\mu_0 \quad (14)$$

where, B denotes the strength of the magnetic field, r denotes the distance from the conductor to the sensor for detecting the magnetic field, and $\mu_0$ denotes the permeability of vacuum.

According to the equation (14), the allowable current $I_{max}$ is 45 mA, assuming that r is 0.05 m and the allowable maximum magnetic field B is 180 nT when the maximum voltage of the circuit is 10 V. As such, setting the allowable current $I_{max}$ in this embodiment to be 1 mA is not only safe for the subject but also is small enough to permit the SQUID output to be amplified 10 times without saturation.

The measuring results of the invention will be explained further in details.

Figure 4A:
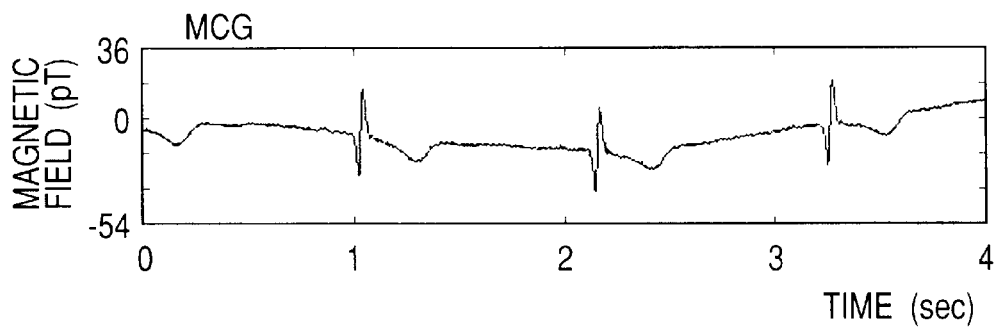
FIG. 4A is a magneto-cardiogram waveform (MCG) detected by the SQUID magnetometers which are placed over the xiphisternum.
Figure 4B:
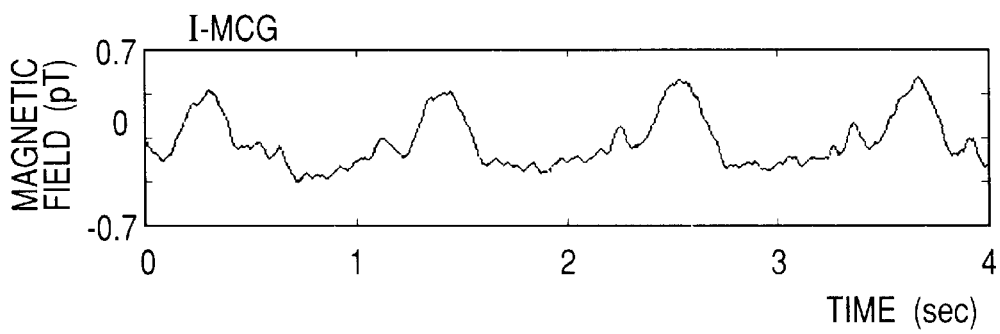
FIG. 4B is an impedance magneto-cardiogram waveform (I-MCG)
Figure 4C:
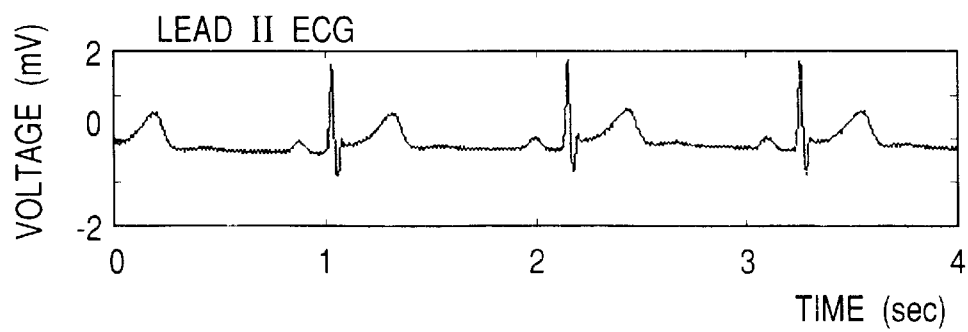
FIG. 4C is a second lead electrocardiogram (Lead II ECG)

Measurements in this embodiment of the present invention provide waveforms displayed on the display unit, as typically shown in FIG. 4. FIG. 4A is a magneto-cardiogram waveform (MCG) measured by the SQUID magnetometer placed over the xiphisternum. FIG. 4B is an impedance magneto-cardiogram waveform (I-MCG). FIG. 4C is a second lead electrocardiogram (Lead II ECG) as reference signals recorded simultaneously with MCG and I-MCG. The x axis in FIGS. 4A to 4C represents time (in second), and the y axis in FIGS. 4A and 4B represents the strength of magnetic fields (in pT) and in FIG. 4C represents voltage (in mV).

It is noted that the waveform of MCG as well as I-MCG changes synchronized with the heart beats of the subject. The peak of R-wave in Lead II ECG is used as a triggering signal for the averaging process.

In the embodiment of the present invention, a diagnosis is carried out on a healthy body subject to obtain I-MCG and MCG simultaneously at 64 points. The waveforms of I-MCG are displayed on the display unit as shown in FIG. 5A, and the waveforms of MCG are displayed on the display unit as shown in FIG. 5B.

Figure 5A:
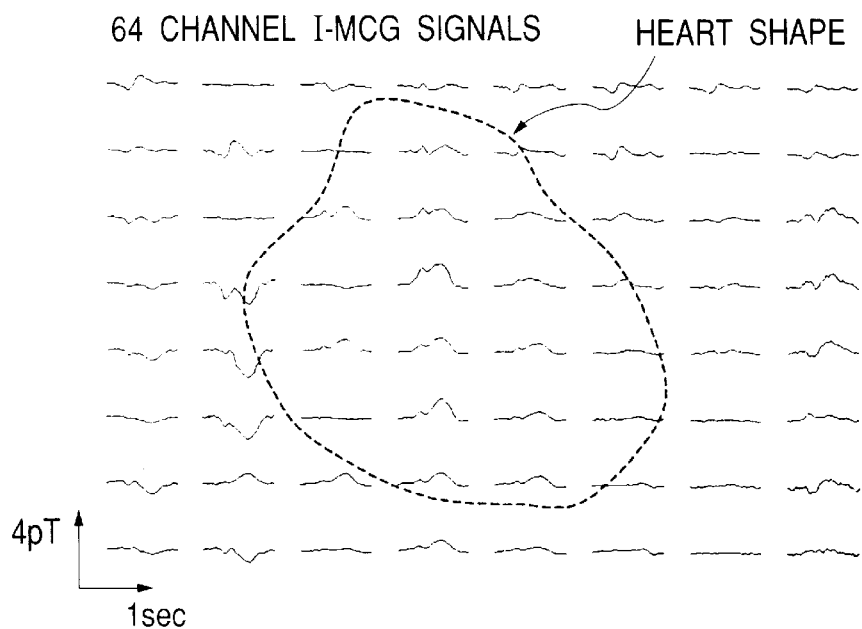
FIGS. 5A and 5B show respectively impedance magneto-cardiogram waveforms (I-MCG) and magneto-cardiogram waveforms (MCG) taken at 64 spots on a healthy subject.
Figure 5B:
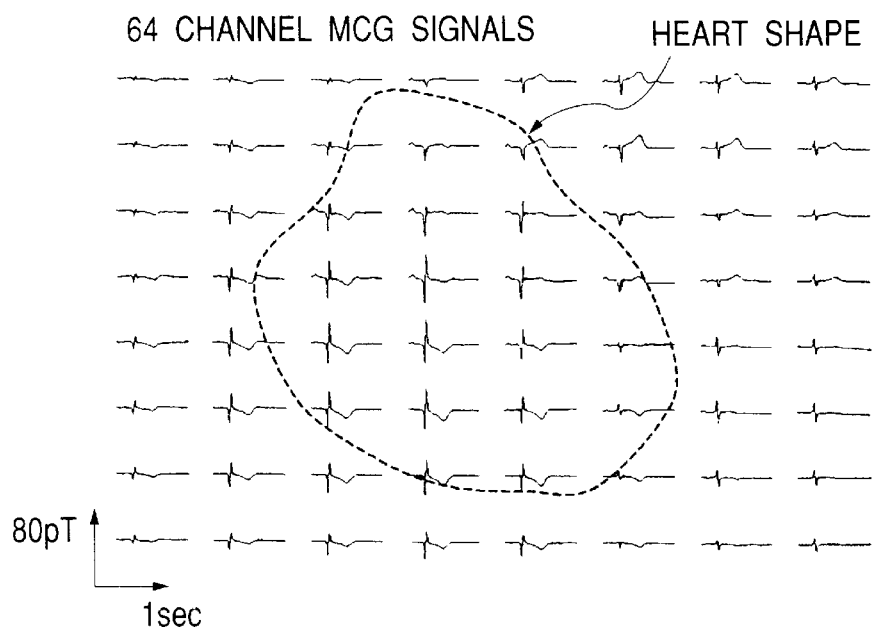

In FIGS. 5A and 5B, the x axis represents time (in s) and the y axis represents the strength of magnetic fields (pT). The measurement is carried out on the subject which deepbreathes every 15 seconds. The measured ten repetitive raw data (waveforms) at each measuring point are added and divided by ten during a time period while the trigger signal of the R-wave in Lead II ECG measured at the same time. A starting time of each of the repetitive waveforms of MCG and I-MCG obtained at each measuring point shown in FIG. 2B is determined on the basis of Lead II ECG which is measured simultaneously with I-MCG and MCG.

FIGS. 5A and 5B also show the outline of the heart obtained from an MRI image for reference to the respective positions of the measuring points and the heart. It is noted in FIG. 5A that negative waveforms appear near the right wall of the right ventricle and positive waveforms appear near the ventricular septum. On the other hand, the waveforms in FIG. 5B are identical to the known magnetocardiogram waveforms. This indicates that the high-frequency current produces no effect on the subject.

Figure 6A:
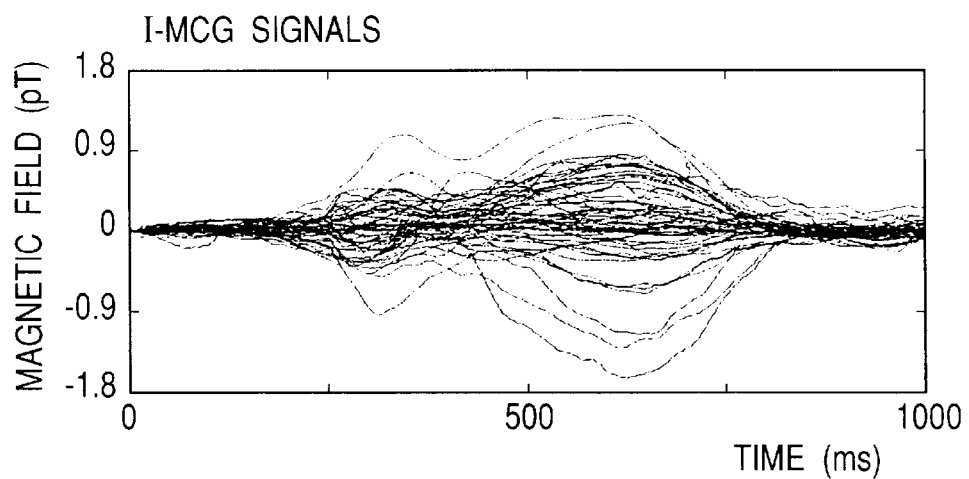
FIGS. 6A and 6B show respectively the over-lapping impedance magneto-cardiogram waveforms (I-MCG) and the over-lapping magneto-cardiogram waveforms (MCG) taken at the same 64 spots as in FIG. 5.
Figure 6B:
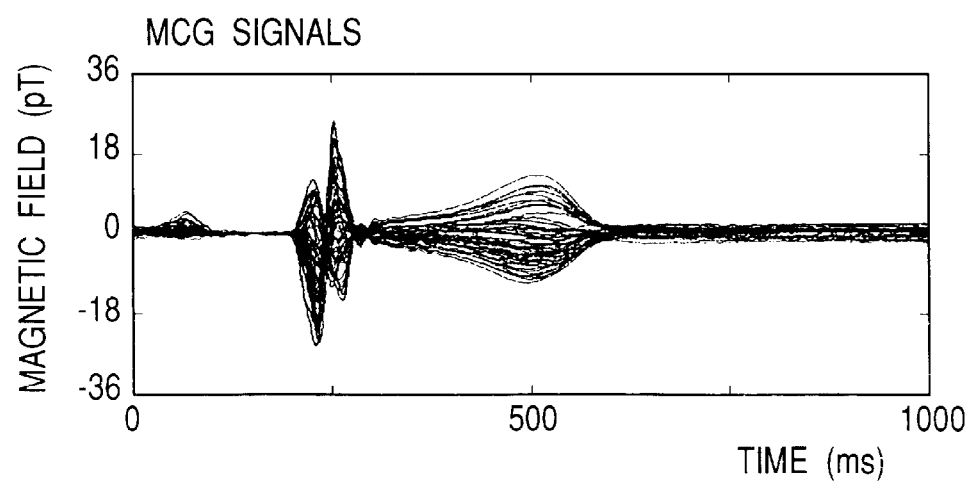

In the embodiment of the present invention, measurements are taken on a healthy subject to obtain I-MCG and MCG simultaneously at 64 points. The overlapping waveforms of I-MCG are shown in FIG. 6A, and the overlapping waveforms of MCG are shown in FIG. 6B. In FIGS. 6A and 6B, the x axis represents time (in ms) and the y axis represents the strength of magnetic fields (pT).

In order to observe how I-MCG and MCG change along with time, the 64 waveforms of I-MCG in FIG. 5 overlap in FIG. 6A and the 64 waveforms of MCG in FIG. 5 overlap in FIG. 6B.

It is noted that T-wave of MCG appears near 500 ms in FIG. 6B and a large peak of I-MCG appears after T-wave in FIG. 6A. It is also noted in FIG. 6A that small peaks appear before large peaks near 300 ms. It is considered that the trough (near 400 ms) between the peaks near 300 ms and 600 ms in FIG. 6A corresponds to the period in which the aortic valve or pulmonary valve opens, or the tricuspid valve or the mitral valve closes. Therefore, the waveform near 600 ms reflects the change in the volume of the ventricle or the impedance of the entire ventricle, and the waveform near 300 ms reflects the change in the volume of the atrium or the impedance of the entire atrium.

Figure 7A:
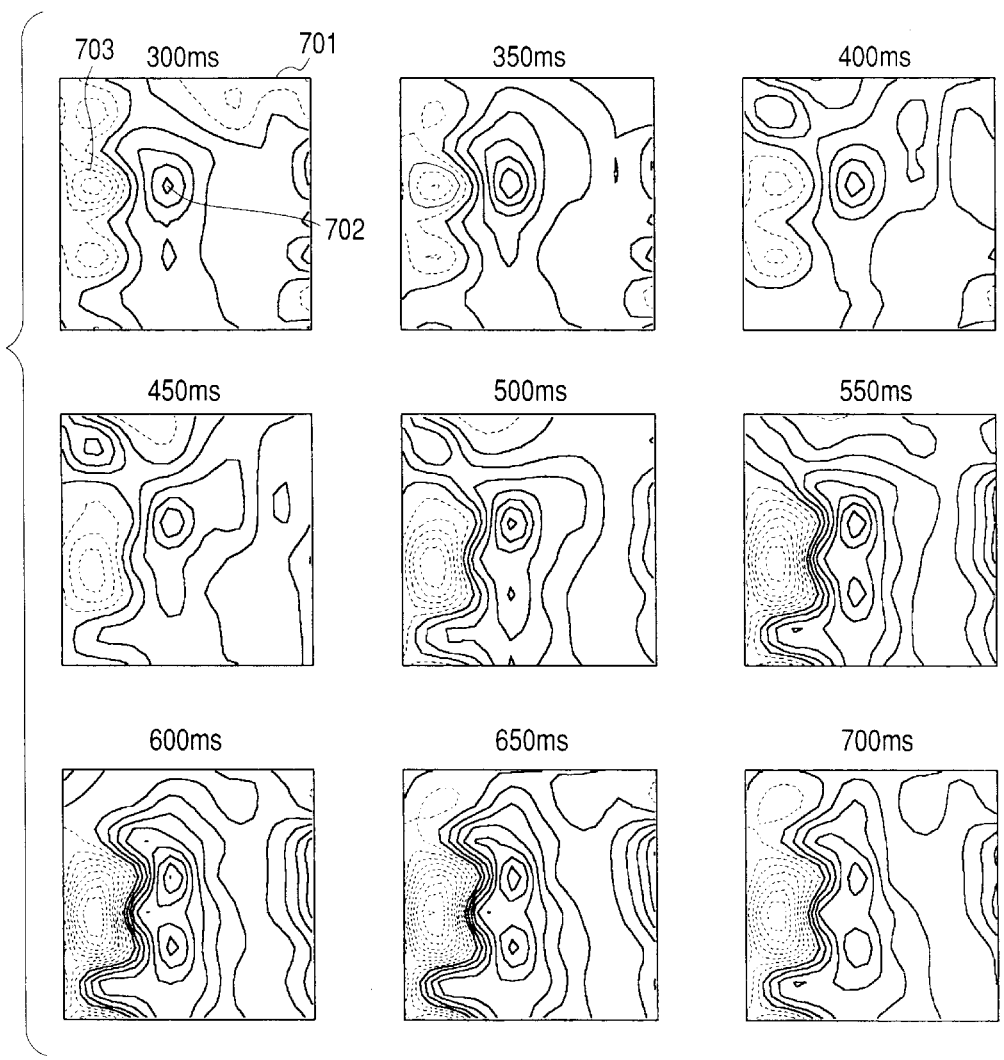
FIG. 7A shows two-dimensional contour maps changing with time.
Figure 7B:
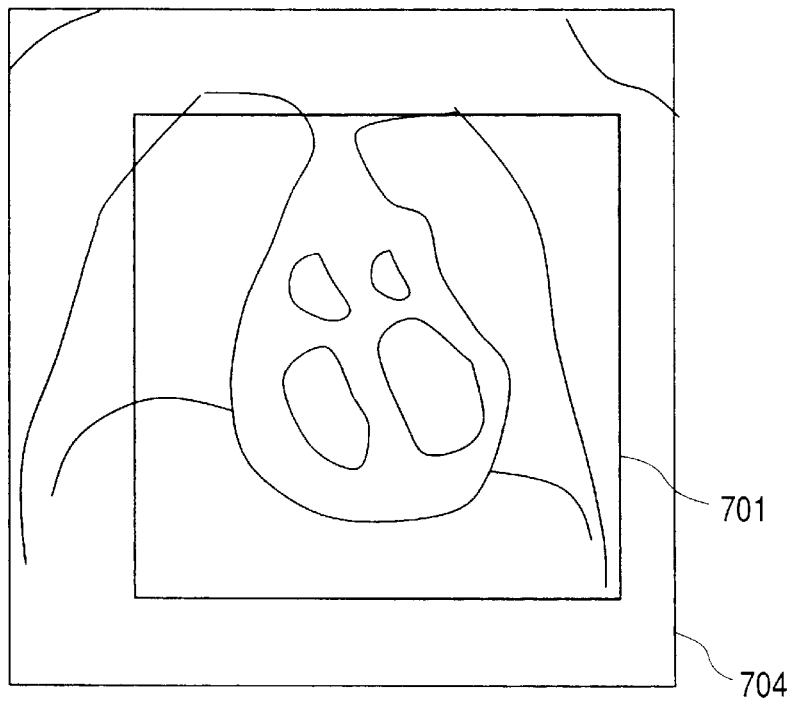
FIG. 7B shows the area for I-MCG measurement in the MRI image.
Figure 7C:
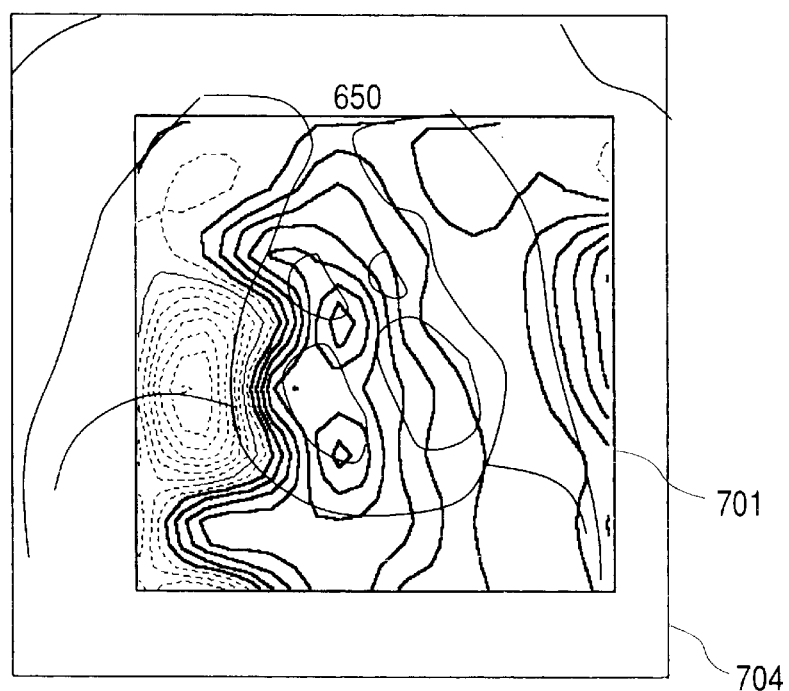
FIG. 7C shows one impedance magneto-cardiogram waveform (I-MCG) of FIG. 7A which overlaps the MRI image of FIG. 7B.

The I-MCG shown in FIGS. 5 and 6 have been made into two-dimensional contour maps which are displayed on the display unit as shown in FIG. 7. FIG. 7A shows two-dimensional contour maps of the waveforms which vary with time from 300 ms to 700 ms in FIG. 6A. In FIG. 7B, the I-MCG (701) overlaps the coronal MRI image (704). In FIG. 7C, the I-MCG map (701) overlaps the MRI image (704).

In FIGS. 7A to 7C, "701" denotes the area of measurement within 210×210 mm shown in FIG. 2B. The solid line indicates the plus contour line (702) and the broken line indicates the minus contour line (703).

FIG. 7C is intended to indicate the relative positions of the heart and the I-MCG map. To this end, the MRI image overlaps the contour map obtained from the waveform at 650 ms in the I-MCG shown in FIG. 5A and FIG. 6A. The MRI image is taken by spin-echo sequence with 1.5 Tesla.

It is noted in FIG. 7A that a positive peak (center of source of a magnetic field) appears near the right atrium before 450 ms and another positive peak appears near the right ventricle after 500 ms. The negative contour line 703 reaches its peak at the far right side of the right ventricle or right atrium. However, the contour line does not appear beside the left ventricle or the left atrium.

A possible explanation for the peak appearing beside the right ventricle and the right atrium is that the right ventricle and the right atrium located at a place near the pickup coil of the SQUID magnetometer, as inferred from the structure of the heart.

Figure 8A:
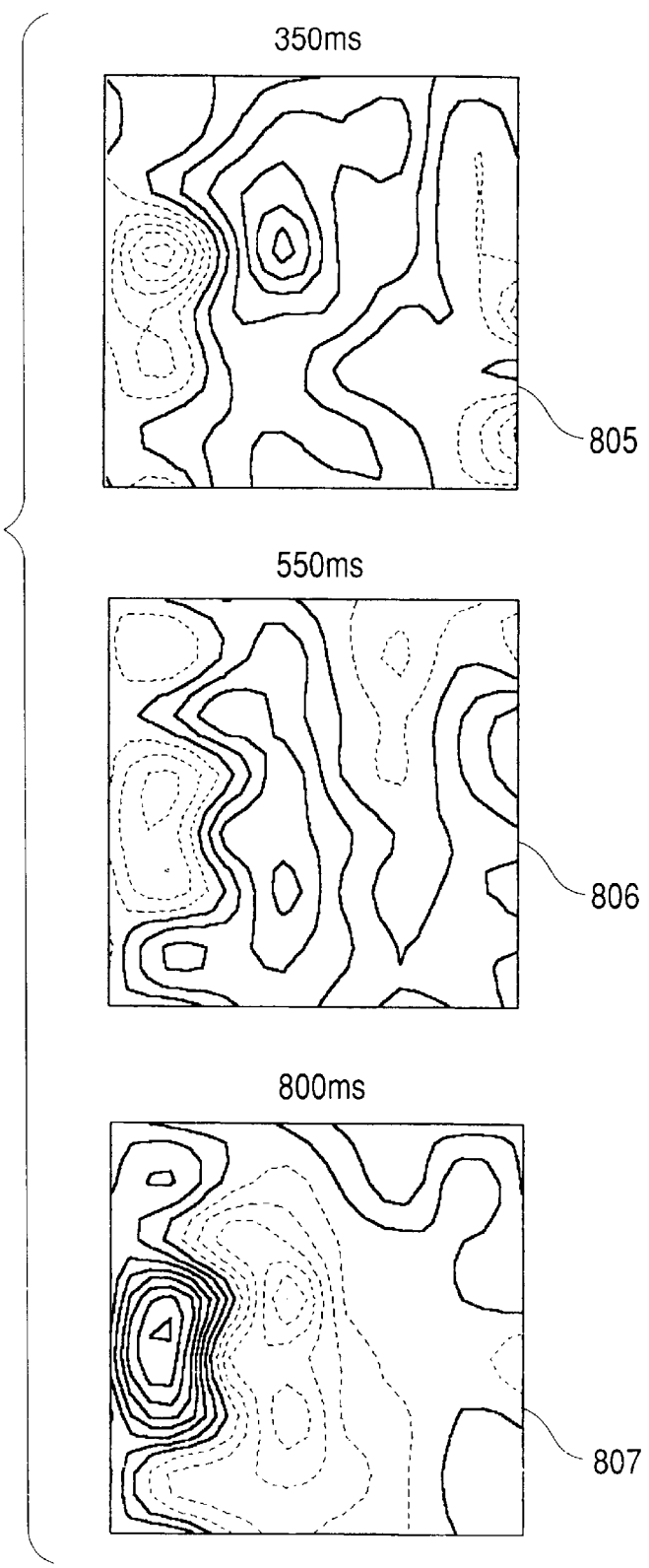
FIGS. 8A and 8B show respectively a map and a time-differential waveform obtained from the impedance magneto-cardiogram waveforms (I-MCG) shown in FIGS. 5A and 6A.
Figure 8B:
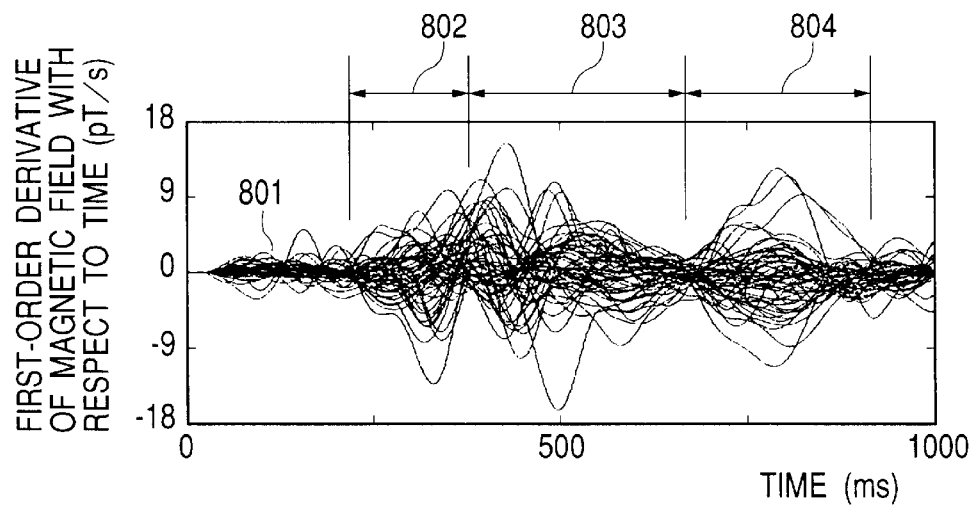

FIG. 8B shows a superposition (801) of first-order derivatives calculated by the computer from the 64-channel I-MCG signals shown in FIGS. 5 and 6. In FIG. 8B, the x axis represents time (in ms) and the y axis represents first-order derivative of strength of magnetic fields with respect to time (in pT/s). FIG. 8A is a map showing the first-order time derivatives of the waveforms shown in FIG. 8B.

The first-order derivatives 801 shown in FIG. 8B may overwrite the 64-channel I-MCG signals in FIG. 5A. Alternatively, the first-order derivatives 801 may be displayed on the display unit in correspondence with the place where the pickup coils of the SQUID magnetometer are arranged.

The first-order derivatives may be obtained by means of hardware, such as an analog circuit, rather than the software of digital computation. In this case the analog circuit is constructed by connecting a differentiating circuit to the band-pass filter 34 or amplifier 35 shown in FIG. 3.

FIG. 8A is a map drawn by connecting points having an equal time derivatives on the waveforms in FIG. 8B. Maps 805, 806, and 807 correspond respectively to the time 350 ms, 550 ms, and 800 ms respectively representing the systole of the atrium 802, the systole of the ventricle 803, and the diastole of the ventricle 804. In FIG. 8A, the solid line indicates the positive contour line and the broken line indicates the negative contour line.

The waveforms reflecting impedance changes are differentiated with respect to time by the same method used for measuring potential with impedance cardiogram. This method is effective in observing the diastole period, the rapid filling period, the systole period, and the ejection period of a heart beat.

FIG. 8B reflects three phases of a heartbeat—the systole of atrium the 802, the systole of the ventricle 803, and the diastole of the ventricle 804—which can be distinguished from one another. The map 805 corresponding to the systole of the atrium 802, which has a plus peak at the position of the right atrium. The map 806 corresponding to the systole of the ventricle 803, which has a plus peak in the vicinity of the right ventricle. The map 807 corresponding to the diastole of the ventricle 804, which has a minus peak (center of sink of the magnetic field) in the vicinity of the right ventricle. The pattern of map 806 is the reverse of the pattern in map 807.

Figure 9A:
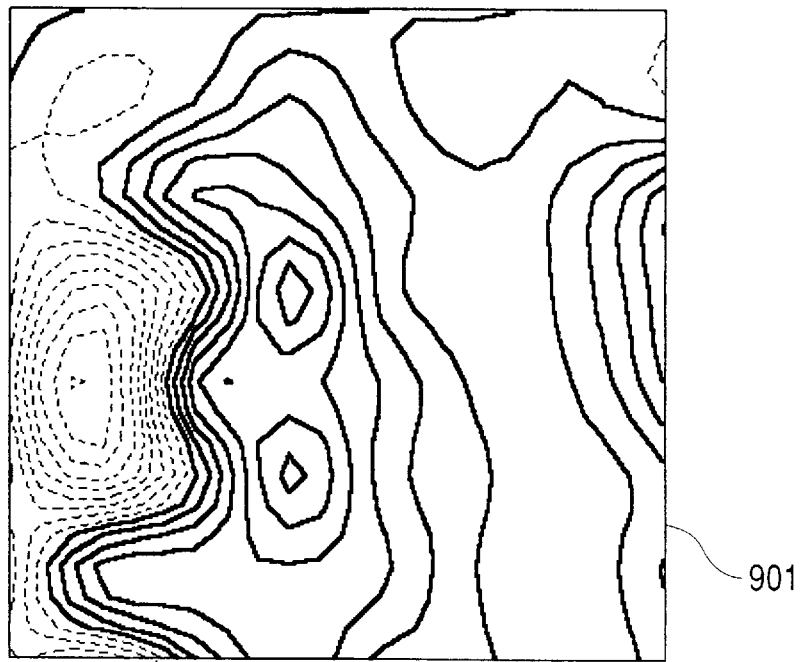
FIGS. 9A to 9C show respectively a contour map obtained from I-MCG, a current arrow map obtained from FIG. 9A, and an area for measurement shown in the MRI image.
Figure 9B:
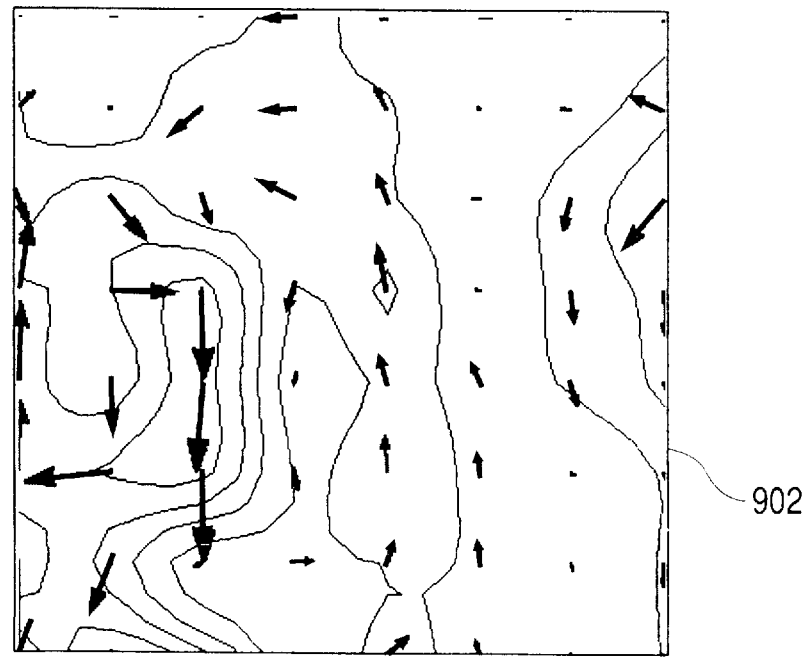
Figure 9C:
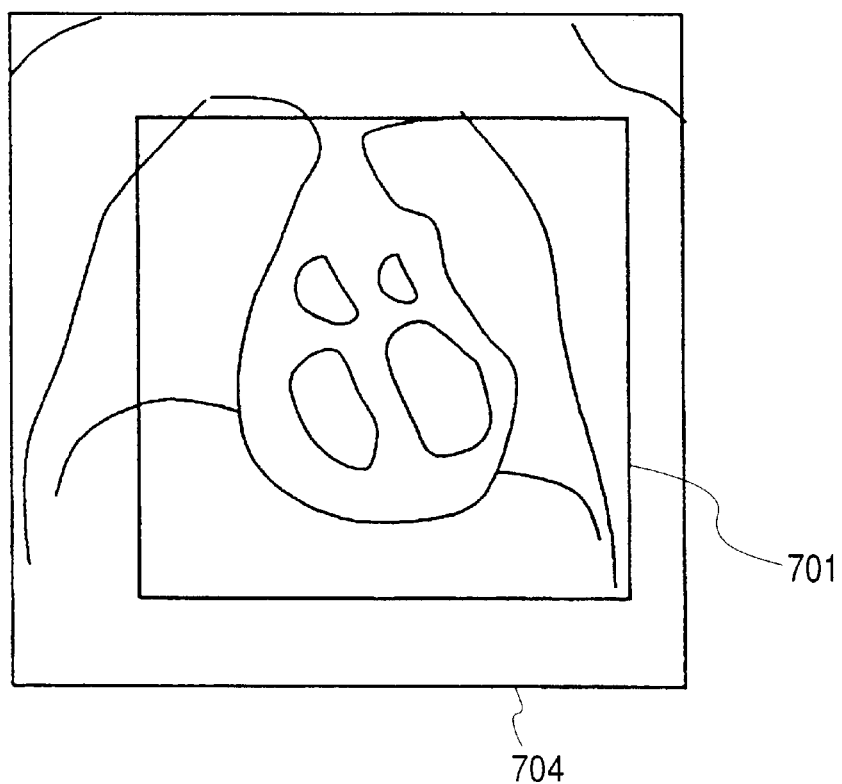

In the embodiment of the present invention, the display unit displays a contour map obtained from I-MCG as shown in FIG. 9A, a current arrow map obtained from the contour map in FIG. 9A as shown in FIG. 9B, and a range of measurements indicated by MRI image as shown in FIG. 9C. FIG. 9A is a two-dimensional contour map 901 at 650 ms in FIGS. 7A and 7C obtained from I-MCG. FIG. 9B is a current arrow map prepared from FIG. 9A. FIG. 9C shows the range 701 for measuring of I-MCG which overlaps the coronal MRI image 704, as in the case of FIG. 7B.

In FIG. 9A, the solid line indicates the positive contour line and the broken line indicates the negative contour line. FIG. 9B is a current arrow map which shows current arrows ($I_x,I_y$) as arrow vectors on the (x, y) plane overlapping a contour map of contour lines connecting points with equal $I_{xy}$ values on the (x, y) plane. The current arrows ($I_x,I_y$) are determined by the values $I_x$ and $I_y$ which are obtained by partial differentiating the magnetic field $B_z$ (shown by the two-dimensional contour map) with respect to x and y according to the equations 15 and 16. The value of $I_{xy}$ is calculated according to the equation 17.

$$I_x = \partial B_z/\partial y \quad (15)$$

$$I_y = -\partial B_z/\partial x \quad (16)$$

$$I_{xy} = \sqrt{(I_x^2 + I_y^2)} \quad (17)$$

It appears in the current arrow map 902 shown in FIG. 9B that strong current appears in the area corresponding to the right wall of the right ventricle. It is known that weak current appears around the wall of the right ventricle, and strong current appears the right wall of the right ventricle, and weak current appears near the left wall of the left ventricle. These results suggest that it is possible to estimate the approximate position of the heart by using the current arrow map. This will be discussed later in details with reference to FIG. 11.

Figure 10A:
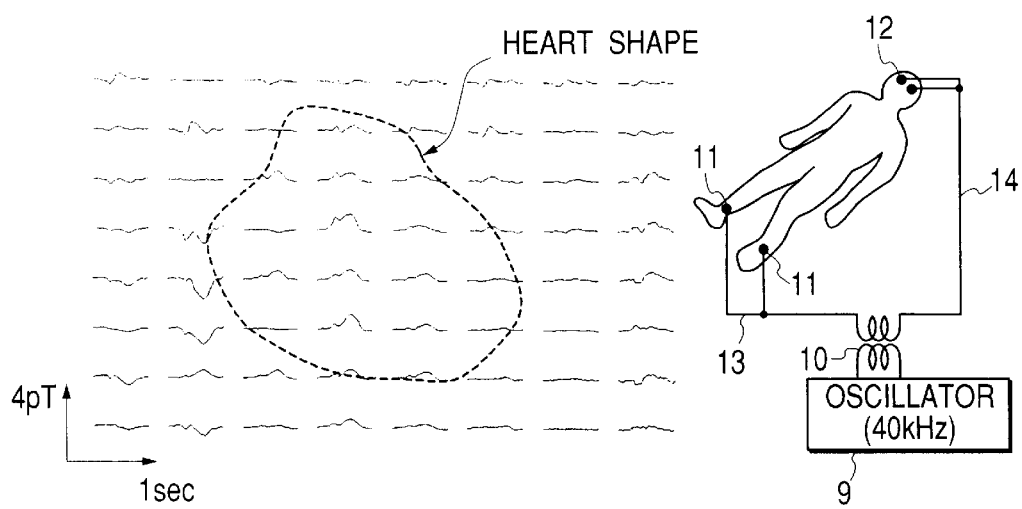
FIG. 10A shows the measurements with electrodes attached to the forehead and both ankles of a human body.
Figure 10B:
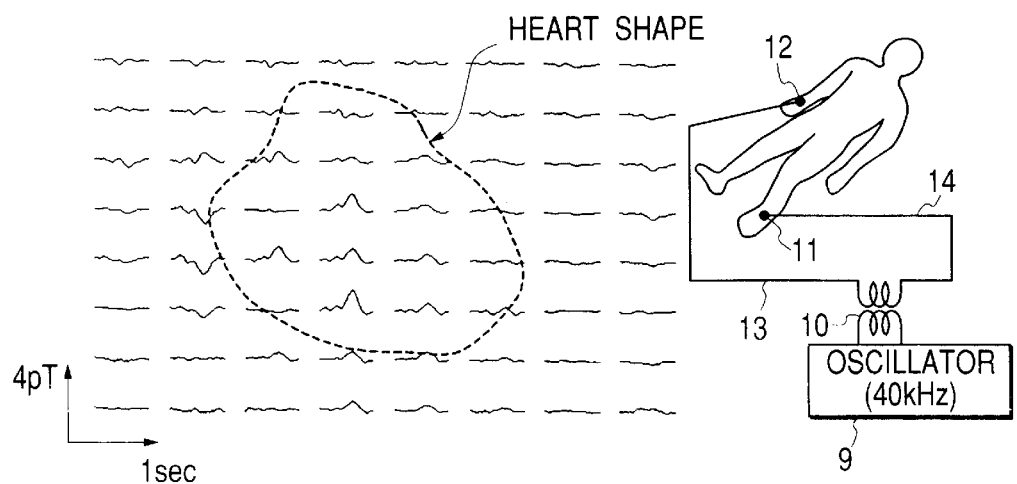
FIG. 10B shows the measurements with electrodes attached to both wrists and both ankles of the human body.

FIG. 10 shows how the results change along with the changes of the arrangement of electrodes. FIG. 10A shows I-MCG obtained by measuring with two electrodes attached to the forehead and two electrodes each attached to an ankle. The I-MCG is identical with that shown in FIG. 5A. FIG. 10B shows I-MCG obtained by measuring with two electrodes attached to the forehead, one electrode 12 attached to the right wrist, and one electrode 11 attached to the left ankle. The I-MCG in FIGS. 10A and 10B was obtained by measuring at 64 points, with the x axis representing time (in s) and the y axis representing the strength of magnetic field (in pT).

There is no appreciable difference between FIGS. 10A and 10B in the positions where the positive waveforms and the negative waveforms appear. However, for the polarity of waveforms at the left side of the left ventricle, slight difference is noticed between FIGS. 10A and 10B which may be caused by the difference in the arrangement of electrodes 11 and 12. Symmetrical arrangement of electrodes as shown in FIG. 10A appears to be more effective for high-frequency current flowing uniformly through the subject.

Figure 11:
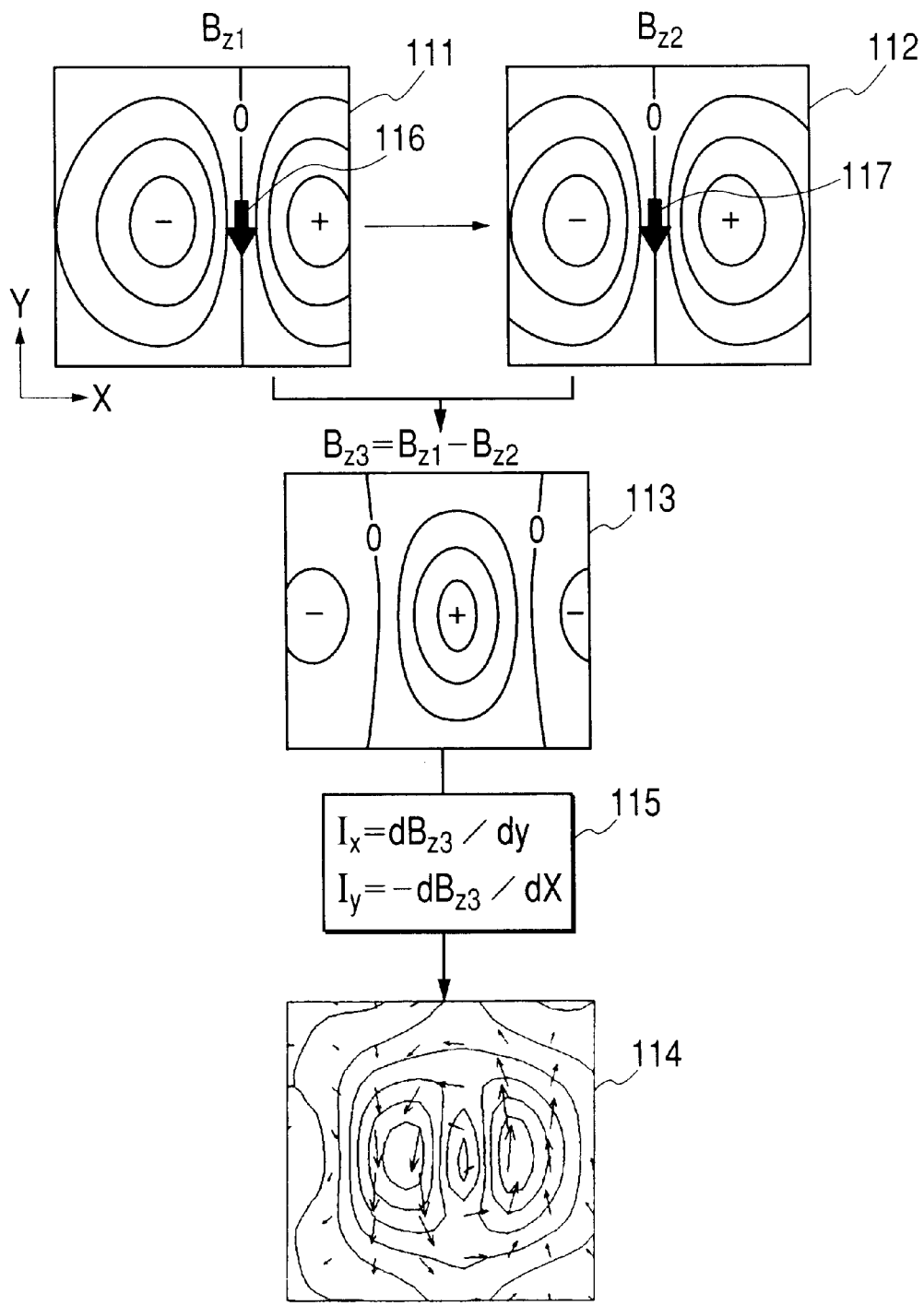
FIG. 11 shows a contour map obtained from the impedance magneto-cardiogram waveforms (I-MCG) and a simple simulation of the current arrow map for the embodiment shown in FIG. 1.

The contour map and the current arrow map obtained from I-MCG are examined by a simple simulation. The results are shown in FIG. 11. The symbol "+" denotes the center of a source of the magnetic field and the symbol "−" denotes the center of a drain of the magnetic field. The straight or curved line with "0" is a contour line representing the zero strength of the magnetic fields.

It is assumed that the current source 116 in the contour map 111 (distribution of equal magnetic field magnitudes with respect to $B_{z1}$) obtained from I-MCG changes into the current source 117 in the contour map 112 (distribution of equal magnetic field magnitudes with respect to $B_{z2}$), with its magnitude and depth remaining the same. The change takes place because the high-frequency current flowing through the subject varies the conductivity so as to move the current channel in the x direction by 30 mm. In the case of the simulation in FIG. 11, it is also assumed that the current source is at a depth of 80 mm from the pickup coil.

The contour map 113 obtained under the above-mentioned assumption shows $B_{z3}=B_{z1}-B_{z2}$ because that the magnetic field tested is the amount of change in magnetic fields. It is known from the contour map 113 that there is a plus peak at the intermediate position between the current sources 116 and 117. The current arrow map 114 is obtained based upon the magnetic field $B_{z3}$ in the contour map 113 by calculating according to the equations 15, 16, and 17. It is known from the current arrow map 114 that the peaks appear along the change of current and current flows in a circular direction.

The foregoing suggests that the distribution of magnetic fields in the normal direction or the distribution of equal magnetic field magnitudes makes the peaks appear near the place where the conductivity changes, which suggests that the current arrow map represents the profile of the place where the conductivity changes.

Based upon the above discussion, the peak in the two-dimensional contour map in FIG. 7 represents the right atrium and the right ventricle, and the current component of the current arrow map in FIG. 9 represents the right wall of both the right atrium and the right ventricle as well as the left wall of both the septum and the left ventricle.

As mentioned above, the embodiment of the present invention enables one skilled in the art to measure in real time the cardiac magnetic fields while applying a high-frequency current to the live body and to detect in real time the mechanical movement of the heart which is induced by the blood flow through the heart.

The charts of magnetic fields distribution shown in FIGS. 7 and 8 enable one skilled in the art to estimate the current source in the live body by using the Biot-Savert law and the method of least squares, or to estimate the current distribution by using the lead field matrix. The estimated current source enables one skilled in the art to estimate the change of the conductivity or the resistivity. These estimates may be displayed in the form of charts showing the distribution of current, conductivity or resistivity, optionally in combination with MRI images.

The waveforms of magnetic fields at the points of measurements and the outline of the heart shown in FIGS. 5 and 10 are collated with the chest of the subject such that the points of the chest are projected onto the chart, when the back of the chart faces downward. Likewise, the two-dimensional maps which are shown in FIGS. 7, 8, 9, and 11 are collated with the chest of the subject such that the points of the chest are projected onto the chart, when the back of the chart faces downward.

The principles, preferred embodiments and modes of operation of the present invention have been described in the foregoing specification. However, the invention which is intended to be protected is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An apparatus for measuring bio-magnetic fields for creating a contour map and an arrow map comprising: a plurality of magnetometers for detecting magnetic fields generated from a live body; a driving circuit for driving said magnetometers; a computer for collecting output signals of said driving circuit in the form of data representing at least one waveform of magnetic fields generated from the live body and for performing an arithmetic processing on said data representing the waveform of magnetic fields; a display unit; a first and a second signal processing circuits for processing output signals of said driving circuit; a signal generator for generating high-frequency AC current adapted to be applied to the live body; and an electric wire for transmitting said high-frequency AC current from said signal generator to the live body via a plurality of electrodes adapted to be attached to a plurality of points on the live body; wherein said first signal processing circuit has a first band-pass filter for passing a first predetermined bandwidth portion of the output signals of said driving circuit, a filter for removing at least one predetermined frequency portion from output signals of said first band-pass filter, and a first amplifier for amplifying output signals of said filter, said second signal processing circuit has a high-pass filter for passing a high bandwidth of the output signals of said driving circuit, a phase-shift detector for demodulating a portion with a frequency of said signal generator from output signals of said high-pass filter, a second band-pass filter for passing a second predetermined bandwidth portion of output signals of said phase-shift detector, and a second amplifier for amplifying output signals of said second band-pass filter, and said display unit displaying at least one of the output signal of said first signal processing circuit and the output signal of said second signal processing circuit.

2. The apparatus for measuring bio-magnetic fields as defined in claim 1, wherein said display unit displays the output signals of said second signal processing circuit in correspondence with positions where said SQUID magnetometers are adapted to be arranged.

3. The apparatus for measuring bio-magnetic fields as defined in claim 1, wherein said electrodes are adapted to be attached to the head and both ankles of the live body.

4. The apparatus for measuring bio-magnetic fields as defined in claim 1, wherein the computer performs an averaging process on the output signals of said second signal processing circuit, which include a plurality of repetitive waveforms, by adding the repetitive waveforms then dividing results of the adding step by the number of the repetitive waveforms during a time period, a starting time and an ending time of the time period are determined based on trigger signals extracted from electrocardiograph measured during the same time period or based upon trigger signals extracted from the output signals of the first signal processing circuit measured during the same time period.

5. The apparatus for measuring bio-magnetic fields as defined in claim 1, wherein the computer performs an arithmetic processing of partial differentiation on the magnetic fields $B_z$ in a z direction which is generally perpendicular to a x, y plane wherein the x, y plane is a front surface of the live body above which the magnetometers are adapted to be arranged, the computer also performs an arithmetic processing for forming from the resulted partial differentials $\partial B_z/\partial x$ and $\partial B_z/\partial y$, the contour map by connecting points of each equal $\sqrt{\{(\partial B_z/\partial x)^2+(\partial B_z/\partial y)^2\}}$ magnitude value respectively at a predetermined time, the computer selectively performs an arithmetic processing for forming the arrow map representing current arrows having $I_x=\{\partial B_z/\partial x\}$ as an x component and $I_y=-\{\partial B_z/\partial y\}$ as a y component at the predetermined time by connecting points with each equal $I_{xy}=\sqrt{(I_x^2+I_y^2)}$ magnitude value, and said contour map and said arrow map are selectively displayed on said display unit.

6. The apparatus for measuring bio-magnetic fields as defined in claim 1, wherein the computer performs an arithmetic processing of first-order differentiation on the waveform of the magnetic fields in a z direction with respect to time so as to generate at least one first-order differential waveform of the magnetic fields to be displayed on said display unit, the waveform of magnetic fields is outputted from said second signal processing circuit, and the z direction is generally perpendicular to a x, y plane and x, y plane is a front surface of the live body above which the magnetometers are adapted to be arrange.

7. The apparatus for measuring bio-magnetic fields as defined in claim 1, wherein the computer performs an arithmetic processing of first-order differentiation on the waveform of the magnetic fields in a z direction with respect to time which is outputted from said second signal processing circuit so as to generate at least one first-order differential waveform of the magnetic fields to be displayed in a overlapping manner on said display unit, and the z direction is generally perpendicular to a x, y plane and the x, y plane is a front surface of the live body above which the magnetometers are arranged.

8. The apparatus for measuring bio-magnetic fields as defined in claim 1, wherein the computer performs an arithmetic processing of first-order differentiation on the waveform of the magnetic fields in a z direction with respect to time which is outputted from said second signal processing circuit so as to generate at least one first-order differential waveform of the magnetic fields, the computer also performs an arithmetic processing for forming the map by connecting points which have equal magnitude of said first-order differential waveform of the magnetic fields at a predetermined time so as to display said map on said display unit, and the z direction is generally perpendicular to a x, y plane and the x, y plane is a front surface of the live body above which the magnetometers are arranged.

9. The apparatus for measuring bio-magnetic fields as defined in claim 1, wherein the computer performs an arithmetic processing of first-order differentiation on the magnetic fields $B_z$ in a z direction with respect to time which is outputted from said second signal processing circuit so as to generate at least one first-order differential waveform $B_z'$ of the magnetic fields, the computer performs an arithmetic processing of partial differentiation on said first-order differential waveform $B_z'$ of the magnetic fields with respect to an x variable in an x direction and a y variable in a y direction so as to generate at least one pair of partial differentials $\partial B_z'/\partial_x$ and $\partial B_z'/\partial_y$ of the magnetic fields, the computer performs an arithmetic processing for forming from said partial differentials $\partial B_z'/\partial_x$ and $\partial B_z'/\partial_y$ the contour map by connecting points with an equal $\sqrt{\{(\partial B_z'/\partial_x)^2+(\partial B_z'/\partial_y)^2\}}$ value at a predetermined time, the computer selectively performs an arithmetic processing for forming the arrow map representing current arrows having $I_x=\{\partial B_z/\partial_x\}$ as an x component and $I_y=-\{\partial B_z'/\partial_y\}$ as a y component at the predetermined time by connecting points with each equal $I_{xy}=\sqrt{(I_x^2+I_y^2)}$ magnitude value, said contour map and said arrow map are selectively displayed on said display unit, and the z direction is generally perpendicular to a x, y plane and the x, y plane is a front surface of the live body above which the magnetometers are arranged.

10. The apparatus for measuring bio-magnetic fields as defined in claim 1, wherein the computer performs an arithmetic processing of partial differentiation on the waveform of the magnetic fields $B_z$ in a z direction with respect to an x variable in an x direction and a y variable in a y direction so as to generate at least one pair of partial differentials $\partial B_z'/\partial_x$ and $\partial B_z'/\partial_y$ of the magnetic fields, the computer performs an arithmetic processing for forming from said partial differentials $\partial B_z'/\partial_x$ and $\partial B_z'/\partial_y$ the contour map by connecting points with an equal $\sqrt{\{(\partial B_z'/\partial_x)^2+(\partial B_z'/\partial_y)^2\}}$ value at a predetermined time, the computer performs an arithmetic processing for estimating at least one current dipole to be displayed on said display unit by using said contour map, the waveform of the magnetic fields $B_z$ are outputted from said second signal processing circuit, and the z direction is generally perpendicular to a x, y plane and the x, y plane is a front surface of the live body above which the magnetometers are adapted to be arranged.

11. The apparatus for measuring bio-magnetic fields as defined in claim 1, wherein the computer performs an arithmetic processing of first-order differentiation on the waveform of the magnetic fields $B_z$ in a z direction with respect to time which is obtained as the output signals of said second signal processing circuit so as to generate at least one first-order differential waveform $B_z'$ of the magnetic fields, the computer performs an arithmetic processing of partial differentiation on the waveform of the magnetic fields $B_z$ in a z direction with respect to an x variable in an x direction and a y variable in a y direction so as to generate at least one pair of partial differentials $\partial B_z'/\partial_x$ and $\partial B_z'/\partial_y$ of the magnetic fields, the computer performs an arithmetic processing for forming from said partial differentials $\partial B_z'/\partial_x$ and $\partial B_z'/\partial_y$ the contour map by connecting points with an equal $\sqrt{\{(\partial B_z'/\partial_x)^2+(\partial B_z'/\partial_y)^2\}}$ value at a predetermined time, the computer performs an arithmetic processing for estimating at least one current dipole to be displayed on said display unit by using said contour map, and the z direction is generally perpendicular to a x, y plane and the x, y plane is a front surface of the live body above which the magnetometers are arranged.

12. The apparatus for measuring bio-magnetic fields as defined in claim 1, wherein the computer performs an arithmetic processing of partial differentiation on the waveform of the magnetic fields $B_z$ in a z direction with respect to an x variable in an x direction and a y variable in a y direction so as to generate at least one pair of partial differentials $\partial B_z'/\partial_x$ and $\partial B_z'/\partial_y$ of the magnetic fields, the computer performs an arithmetic processing for forming from said partial differentials $\partial B_z'/\partial_x$ and $\partial B_z'/\partial_y$ the contour map by connecting points with an equal $\sqrt{\{(\partial B_z'/\partial_x)^2+(\partial B_z'/\partial_y)^2\}}$ value at a predetermined time, the computer performs an arithmetic processing for estimating the distribution of conductivity in the live body to be displayed on said display unit, and the z direction is generally perpendicular to a x, y plane and the x, y plane is a front surface of the live body above which the magnetometers are adapted to be arranged.

13. The apparatus for measuring bio-magnetic fields as defined in claim 1, wherein the computer performs an arithmetic processing of first-order differentiation on the waveform of the magnetic fields in a z direction with respect to time which is outputted from said second signal processing circuit so as to generate at least one first-order differential waveform of the magnetic fields, the computer performs an arithmetic processing of partial differentiation on the waveform of the magnetic fields $B_z$ in a z direction with respect to an x variable in an x direction and a y variable in a y direction so as to generate at least one pair of partial differentials $\partial B_z'/\partial_x$ and $\partial B_z'/\partial_y$ of the magnetic fields, the computer performs an arithmetic processing for forming from said partial differentials $\partial B_z'/\partial_x$ and $\partial B_z'/\partial_y$ the contour map by connecting points with an equal $\sqrt{\{(\partial B_z'/\partial_x)^2+(\partial B_z'/\partial_y)^2\}}$ value at a predetermine time, the computer performs an arithmetic processing for estimating the distribution of conductivity in the live body to be displayed on said display unit, and the z direction is generally perpendicular to a x, y plane and the x, y plane is a front surface of the live body above which the magnetometers are adapted to be arranged.

14. The apparatus for measuring bio-magnetic fields as defined in claim 1, wherein the signal generator includes an oscillator.

15. An apparatus for measuring bio-magnetic fields for creating a contour map and an arrow map comprising: a plurality of magnetometers for detecting magnetic fields generated from a live body; a driving circuit for driving said magnetometers; a computer for collecting output signals of said driving circuit in the form of data representing at least one waveform of magnetic fields generated from the live body and for performing an arithmetic processing on said data representing the waveform of magnetic fields; a display unit; a signal processing circuit for processing output signals of said driving circuit; a signal generator for generating high-frequency AC current adapted to be applied to the live body; and an electric wire for transmitting said high-frequency AC current from said signal generator to the live body via a plurality of electrodes adapted to be attached to a plurality of points on the live body; wherein said signal processing circuit has a high-pass filter for passing a high bandwidth of the output signals of said driving circuit, a phase-shift detector for demodulating a portion with a frequency of said signal generator from output signals of said high-pass filter, a band-pass filter for passing a predetermined bandwidth portion of output signals of said phase-shift detector, and an amplifier for amplifying output signals of said band-pass filter, and said display unit displaying the output signal from said signal processing circuit.

16. The apparatus for measuring bio-magnetic fields as defined in claim 15, wherein the computer performs an arithmetic processing of first-order differentiation on the waveform of the magnetic fields in a z direction with respect to time so as to generate at least one first-order differential waveform of the magnetic fields to be displayed on said display unit, the waveform of the magnetic fields is outputted from said signal processing circuit, and the z direction is generally perpendicular to a x, y plane and the x, y plane is a front surface of the live body above which the magnetometers are adapted to be arranged.

17. The apparatus for measuring bio-magnetic fields as defined in claim 15, wherein the computer performs an arithmetic processing of first-order differentiation on the waveform of the magnetic fields in a z direction with respect to time which is outputted from said signal processing circuit so as to generate at least one first-order differential waveform of the magnetic fields to be displayed in a overlapping manner on said display unit, and the z direction is generally perpendicular to a x, y plane and the x, y plane is a front surface of the live body above which the magnetometers are adapted to be arranged.

18. The apparatus for measuring bio-magnetic fields as defined in claim 15, wherein the computer performs an arithmetic processing of first-order differentiation on the waveform of the magnetic fields in a z direction with respect to time which is outputted from said signal processing circuit so as to generate at least one first-order differential waveform of the magnetic fields, the computer also performs an arithmetic processing for forming the map by connecting points which has equal magnitude of said first-order differential waveform of the magnetic fields at a predetermined time so as to display said map on said display unit, and the z direction is generally perpendicular to a x, y plane and the x, y plane is a front surface of the live body above which the magnetometers are adapted to be arranged.

19. The apparatus for measuring bio-magnetic fields as defined in claim 15, wherein the computer performs an arithmetic processing of first-order differentiation on the magnetic fields $B_z$ in a z direction with respect to time which is outputted from said signal processing circuit so as to generate at least one first-order differential waveform $B_z'$ of the magnetic fields, the computer performs an arithmetic processing of partial differentiation on said first-order differential waveform $B_z'$ of the magnetic fields with respect to an x variable in an x direction and a y variable in a y direction so as to generate at least one pair of partial differentials $\partial B_z'/\partial_x$ and $\partial B_z'/\partial_y$ of the magnetic fields, the computer performs an arithmetic processing for forming from said partial differentials $\partial B_z'/\partial_x$ and $\partial B_z'/\partial_y$ the contour map by connecting points with an equal $\sqrt{\{(\partial B_z'/\partial_x)^2+(\partial B_z'/\partial_y)^2\}}$ value at a predetermined time, the computer selectively performs an arithmetic processing for forming the arrow map representing current arrows having $I_x=\{\partial B_z/\partial_x\}$ as an x component and $I_y=-\{\partial B_z/\partial_y\}$ as a y component at the predetermined time by connecting points with each equal $I_{xy}=\sqrt{(I_x^2+I_y^2)}$ magnitude value, said contour map and said arrow map are selectively displayed on said display unit, and the z direction is generally perpendicular to a x, y plane and the x, y plane is a front surface of the live body above which the magnetometers are adapted to be arranged.

20. The apparatus for measuring bio-magnetic fields as defined in claim 15, wherein the signal generator includes an oscillator.

* * * * *